United States Patent [19]
Isbell et al.

[11] Patent Number: 6,051,214
[45] Date of Patent: Apr. 18, 2000

[54] SHAMPOOS AND CONDITIONERS CONTAINING ESTOLIDES

[75] Inventors: Terry A. Isbell, Elmwood; Thomas P. Abbott, Peoria; John A. Dworak, Chicago, all of Ill.

[73] Assignee: The United States of America, as represented by the Secretary of Agriculture, Washington, D.C.

[21] Appl. No.: 09/161,356

[22] Filed: Sep. 25, 1998

[51] Int. Cl.[7] ........................................... A61K 7/075
[52] U.S. Cl. ................... 424/70.21; 424/70.22; 424/70.31
[58] Field of Search .............. 424/70.21, 70.22, 424/70.31

[56] References Cited

U.S. PATENT DOCUMENTS 4,567,037  1/1986  Ciaudelli .
4,639,369  1/1987  Ciaudelli .
5,380,894  1/1995  Burg et al. .............................. 554/219

*Primary Examiner*—Thurman K. Page
*Assistant Examiner*—Alysia Berman
*Attorney, Agent, or Firm*—M. Howard Silverstein; Randall E. Deck; John D. Fado

[57] ABSTRACT

Improved shampoos and conditioners are disclosed which provide enhanced rinseability, wet feel, detangling, dry comb feel, style management, shine and/or body to human hair. This improved performance may be achieved by incorporation of fatty acid estolides into the shampoo or conditioner. Thus, the improved shampoos of this invention include aqueous compositions of a surfactant cleansing agent, and a thickener, in combination with one or more fatty acid estolides. Similarly, the improved conditioners of this invention include aqueous compositions of a hair conditioning agent in combination with one or more fatty acid estolides.

21 Claims, No Drawings

SHAMPOOS AND CONDITIONERS CONTAINING ESTOLIDES

BACKGROUND OF THE INVENTION

1. Field of the Invention

The invention relates to shampoos and conditioners with improved rinseability, wet feel, detangling, dry comb feel, style management, shine, and/or body.

2. Description of the Prior Art

Estolides are a group of oligomeric fatty acids wherein the acyl backbone of the fatty acid contains a secondary ester linkage to a second fatty acid. These compounds have been previously described as being useful as lubricants, greases, plasticizers, printing inks, and in cosmetics. See, for example, Burg et al. U.S. Pat. No. 5,380,894. Estolides have been typically produced from hydroxy fatty acids of castor oil by thermal, acid, or lipase catalyzed reactions. Recently, Burg et al. (ibid) disclosed a process for producing estolides from more readily available unsaturated fatty acids found in a variety of plant oils. More recently, Isbell and Kleiman disclosed an improved process for producing high yields of estolides from unsaturated fatty acids by acid catalysis (1994, J. Amer. Oil Chem. Soc., 71(4):379–383; and U.S. patent application Ser. No. 08/382,554).

At their most elemental level, commercial shampoos for human use contain an aqueous formulation of at least one surfactant for use as a cleansing agent. Unfortunately, shampooing may present disadvantages, such as causing hair to become tangled and difficult to comb, unmanageable, dull, lacking body, rough, and/or leaving a soap residue on the hair. A wide variety of optional components have been described for inclusion in shampoos for improving performance as well as aesthetics and marketability. Hair conditioners, which were once used separately from the shampoo, are now included in many shampoo formulations for restoring the original condition of the hair. These conditioners include, for example, silicones, cationic surfactants and quaternary ammonium compounds, and synthetic cationic polymers. Other components which have been described include moisturizing agents, thickeners or viscosity modifying agents for enhancing hand application, lathering agents for increasing foaming, foam stabilizers, and pearlizing agents. Examples of yet other components which are commonly included include perfumes, pH control agents, colorants, preservatives, and antimicrobials.

SUMMARY OF THE INVENTION

We have now invented improved shampoos and conditioners which provide enhanced rinseability, wet feel, detangling, dry comb feel, style management, shine, and/or body to human hair. This improved performance may be achieved by incorporation of fatty acid estolides into the shampoo or conditioner. Thus, the improved shampoos of this invention include aqueous compositions of a surfactant cleansing agent, and a thickener, in combination with one or more fatty acid estolides. Similarly, the improved conditioners of this invention include aqueous compositions of a hair conditioning agent in combination with one or more fatty acid estolides.

In accordance with this discovery, it is an object of this invention to provide improved shampoos and conditioners with enhanced performance in comparison with commercial shampoos.

Another object of this invention is to provide shampoos and conditioners which provide improved rinseability, wet feel, detangling, dry comb feel, style management, shine, and/or body.

Other objects and advantages of the invention will become readily apparent from the ensuing description.

DETAILED DESCRIPTION OF THE INVENTION

The fatty acid estolides for use herein are generally of the formula (I):

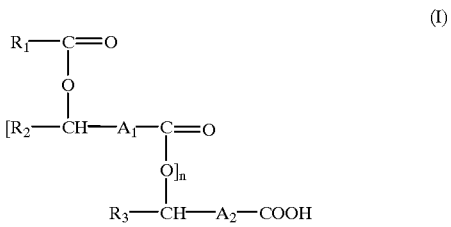

wherein $R_1$, $R_2$ and $R_3$ are independently selected from hydrocarbons which may be saturated or unsaturated, and branched or straight chain, $A_1$ and $A_2$ are independently selected from hydrocarbons which may be saturated or unsaturated, and branched or straight chain, and n is an integer greater than or equal to 0, usually 0 or 1. The estolide is not amidated. Without being limited thereto, preferred estolides include those wherein $R_1$ is a $C_{11}$–$C_{23}$ non-substituted hydrocarbon, $R_2$ and $R_3$ are $C_9$–$C_{19}$ non-substituted hydrocarbons, $A_1$ and $A_2$ are $C_3$–$C_{13}$ non-substituted hydrocarbons, and n is 0 or 1. Particularly preferred estolides include those wherein $R_1$, $R_2$—CH—$A_1$, and $R_3$—CH—$A_2$ are equal.

Estolides for use herein may be prepared from fatty acids using techniques which have been previously described. In the preferred embodiment, the estolides for use herein are produced from unsaturated fatty acids as described by Burg et al. (U.S. Pat. No. 5,380,894, the contents of which are incorporated by reference herein), or Isbell and Kleiman (1994, J. Amer. Oil Chem. Soc., 71(4):379–383; and U.S. patent application Ser. No. 08/382,554, the contents of each of which are also incorporated by reference herein).

Unsaturated fatty acids for use in production of the estolides are naturally occurring in a variety of plant oils and may be conveniently obtained for use therefrom. Meadowfoam oil, having a high content of $\Delta^5$ unsaturated fatty acids including approximately 60% 5-eicosenoic acid (20:1 $\Delta^5$), is preferred as a source of the starting material. In accordance with formula (I), the predominant estolides produced from 5-eicosenoic acid are of the formula wherein $R_1$ is $CH_3(CH_2)_{13}CH=CH(CH_2)_3$—, $R_2$ and $R_3$ are both $CH_3(CH_2)_{14}$—, $A_1$ and $A_2$ are both —$(CH_2)_3$—, and n is between 0–10. Alternatively, oleic acid (18:1 $\Delta^9$), a readily available unsaturated fatty acid, is another preferred starting material. Estolides produced from oleic acid are predominantly of the formula wherein $R_1$ is $CH_3(CH_2)_7CH=CH(CH_2)_7$—, $R_2$ and $R_3$ are both $CH_3(CH_2)8$—, $A_1$ and $A_2$ are both —$(CH_2)_7$—, and n is between 0–10.

The amount of the estolides incorporated into the shampoo or conditioner may vary, but is provided in an amount effective to enhance the performance of the shampoo or conditioner. An effective amount is defined herein as that concentration which is effective to improve one or more of rinseability, wet feel, detangling, dry comb feel, style management, shine, or body of washed hair, relative to control shampoo lacking estolides. Suitable concentrations may be readily determined by routine experimentation and will vary with the specific shampoo or conditioner formulation. However, without being limited thereto, the generally preferred concentration of the estolides in the shampoo or conditioner is between about 1 to 8%, by weight, particularly between about 2 to 6%.

The balance of the shampoo or conditioner may be prepared and formulated using conventional components or agents and water.

Shampoos will include at least one surfactant which is used as a cleansing agent, and a thickener or viscosity modifier. A number of surfactants have been previously described as cleansing agents in shampoos and are suitable for use herein. These include anionic, nonionic, amphoteric, and zwitterionic surfactants, or mixtures thereof. Surfactants which may be used herein include but are not limited to those described by Grote and Russell (U.S. reissue patent no. RE 34,584), Chandler (U.S. Pat. No. 5,554,313), and Glover and Madore (U.S. Pat. No. 5,707,550), the contents of each of which are incorporated by reference herein. The concentration of the surfactant is not critical, but should be effective to be capable of cleaning hair. Generally, suitable concentrations may be between about 1% to about 70%, preferably from about 10% to about 50%. The amount of thickener added also is not critical, but is preferably an amount effective to assist in the hand application of the shampoo. Generally, sufficient thickener is added to raise the viscosity to at least about 1,200 cp at room temperature. Water provides the balance of the shampoo. The concentration of water is not critical, but is usually between about 20% to 95%, preferably from about 40% to 80%.

Ammonium lauryl ether sulfate and coconut diethanolamide (DEA) are particularly preferred surfactants for use in the shampoos of this invention. Specific examples of other suitable anionic surfactants include sodium lauryl sulfate, sodium lauryl ether sulfate, ammonium lauryl sulfate, triethanolamine lauryl sulfate, sodium C14–16 olefin sulfonate, ammonium C12–15 pareth sulfate, sodium myristyl ether sulfate, disodium monooleamidosulfosuccinate, ammonium lauryl sulfosuccinate, sodium dodecylbenzene sulfonate, triethanolamine dodecylbenzene sulfonate, and sodium N-lauryol sarcosinate. Specific examples of amphoteric surfactants which may be used are cocoamphocarboxyglycinate, cocoamphocarboxypropionate, cocobetaine, N-cocamidopropyldimethylglycine, N-lauryl-N-carboxymethyl-N-(2-hydroxyethyl)ethylenediamine; betaines such as alpha-(tetradecyldimethylammonio) acetate, beta-(hexadecyldiethylammonio)propionate, and gamma-(dodecyldimethylammonio)butyrate; and sultaines such as 3-(dodecyldimethylammonio)-propane-1-sulfonate, and 3-(tetradecyldimethylammonio)ethane-1-sulfonate. Examples of nonionic surfactants suitable for use include fatty acid diethanolamides such as isostearic acid DEA, lauric acid DEA, capric acid DEA, linoleic acid DEA, myristic acid DEA, oleic acid DEA, and stearic acid DEA; fatty acid monoethanolamides such as coconut fatty acid monoethanolamide; fatty acid monisopropanolamides such as oleic acid monoisopropanolamide and lauric acid monoisopropanolamide; alkyl amine oxides such as N-cocodimethylamine oxide, N-lauryl dimethylamine oxide, N-myristyl dimethylamine oxide, and N-stearyl dimethylamine oxide; N-acyl amine oxides such as N-cocoamidopropyl dimethylamine oxide and N-tallowamidopropyl dimethylamine oxide; and N-alkoxyalkyl amine oxides such as bis(2-hydroxyethyl) C12-15 alkoxy-propylamine oxide. Examples of zwitterionic surfactants which may be used include 4-[N,N-di(2-hydroxyethyl)-N-octadecylammonio]butane-1-carboxylate, 5-[S-3-hydroxypropyl-S-hexadecylsulfonio]-3-hydroxypentane-1-sulfate, 3-[P,P-diethyl-P-3,6,9-trioxatetradexocylphosphonio]-2-hydroxypropane-1-phosphate, 3-[N,N-dipropyl-N-3-dodecoxy-2-hydroxypropylammonio]-propane-1-phosphonate, 3-(N,N-dimethyl-N-hexadecylammonio)-propane-1-sulfonate, 3-(N,N-dimethyl-N-hexadecylammonio)-2-hydroxypropane-1-sulfonate, 4-[N,N-di(2-hydroxyethyl)-N-(2-hydroxydodecyl)ammonio]-butane-1-carboxylate, 3-[S-ethyl-S-(3-dodecoxy-2-hydroxypropyl)sulfonio] propane-1-phosphate, 3-[P,P-dimethyl-P-dodecylphosphonio]-propane-1-phosphonate, and 5-[N,N-di (3-hydroxypropyl)-N-hexadecylammonio]-2-hydroxypentane-1-sulfate. The above-mentioned surfactants can be used alone or in combination in the shampoos of this invention.

Thickeners have also been previously described for use in shampoos and are suitable for use herein as well. Without being limited thereto, thickening agents which may be used include one or more of sodium alignate; gum arabic; guar gum; hydroxypropyl guar gum; cellulose derivatives such as methylcellulose, hydroxypropyl methylcellulose, hydroxyethylcellulose, carboxymethylcellulose, and hydroxypropylcellulose; starch and starch derivatives such as hydroxyethylamylose and starch amylose; locust bean gum; electrolytes such as sodium chloride and ammonium chloride; saccharides such as fructose and glucose; derivatives of saccharides such as PEG-120 methyl glucose dioleate; diethanolamides of long chain fatty acids; block polymers of ethylene oxide and propylene oxide such as PLURONIC F88 (BASF Wyandotte); polyvinyl alcohol; and ethyl alcohol.

The shampoos may also contain one or more optional components for further improving performance, marketability, or aesthetics, such as conditioners, foaming agents, foam stabilizers, preservatives and/or chelating agents, antimicrobials, fragrances, colorants, opacifiers, pearlizing agents, moisturizing agents, medicaments, buffers and/or pH modifiers, and UV absorbers. The use of these optional components is well known in the art. They are typically added at a level of from about 0.01% to about 10% (each), preferably from about 0.5% to about 5.0%, by weight of the composition.

Many hair conditioning agents have been previously described and are suitable for use herein, including silicones, cationic surfactants and quaternary ammonium compounds, and synthetic cationic polymers. Representative examples of silicon conditioning agents include those described by Grote (RE 34,584) polyalkyl siloxanes such as polydimethyl siloxanes; polyalkylaryl siloxanes such as polymethylphenylsiloxanes; polyether siloxane copolymers such as polypropylene oxide modified dimethylpolysiloxane; and silicone gums such as polydimethylsiloxane, (polydimethylsiloxane) (methylvinylsiloxane) copolymer, poly(dimethylsiloxane) (diphenyl) (methylvinylsiloxane) copolymer, and mixtures thereof. Other silicone fluids which may be used herein are disclosed by Geen (U.S. Pat. No. 2,826,551), Drakoff (U.S. Pat. No. 3,964,500), Pader (U.S. Pat. No. 4,364,837), Woolston (British patent no. 849,433), and Spitzer (U.S. Pat. No. 4,152,416). Other conditioners which may be used include but are not limited to cationic surfactants which contain amino or quaternary ammonium hydrophilic moieties in the molecule which are positively charged, such as quaternary ammonium salts. Specific examples include ditallowdimethyl ammonium chloride, ditallowdimethyl ammonium methyl sulfate, hexadecyl trimethyl ammonium chloride, lauryl trimethyl ammonium chloride, trihexadecyl methyl ammonium chloride, dihexadecyl dimethyl ammonium chloride, di(hydrogenated tallow) dimethyl ammonium chloride, dioctadecyl dimethyl ammonium chloride, dieicosyl dimethyl ammonium chloride, didocosyl dimethyl ammonium chloride, di(hydrogenated tallow) dimethyl ammonium acetate, dihexadecyl dimethyl ammonium acetate, ditallow dipropyl ammonium phosphate, ditallow dimethyl ammonium nitrate, di(coconutalkyl) dimethyl ammonium chloride, and stearyl dimethyl benzyl ammonium chloride. Still other cationic conditioning agents include quaternary nitrogen derivatives of cellulose ethers, homopolymers of dimethyldiallyl ammonium chloride, copolymers of acrylamide and dimethyl diallyl ammonium chloride, homopolymers or copolymers derived from acylic acid or methacrylic acid which contain cationic nitrogen functional groups attached to the polymer by ester or amide linkages, polycondensation products of N,N'-bis-(2,3-epoxypropyl)-piperazine or piperazine-bis-acrylamide and piperazine, and copolymers of vinylpyrrolidone and acrylic acid esters with quaternary nitrogen functionality.

Among the other optional components which may also be included in the shampoo, notable examples include preservatives such as benzyl alcohol, methyl paraben, propyl paraben, formaldehyde, DMDM hydantoin, 5-bromo-5-nitro-1,3-dioxane, sorbic acid, diazolidinyl urea, and imidazolidinyl urea; chelating agents such as disodium ethylenediamine tetraacetate; and pearlizing agents such as ethylene glycol monostearate and ethylene glycol distearate. Suitable pH adjusting agents may include bases such as sodium hydroxide and sodium carbonate; mineral acids such as hydrochloric acid, sulfuric acid, and phosphoric acid; monocarboxylic acids such as acetic acid, lactic acid, and propionic acid; and polycarboxylic acids such as succinic acid, adipic acid, and citric acid.

The composition of a conditioner in accordance with the instant invention may be similar to the shampoo with the exception of the surfactant cleansing agent, which is omitted. Thus, the conditioner will include at least one hair conditioning agent, a thickener, water, and estolide. These components and their formulation may be the same as described hereinabove. However, the amount of water may be increased. As with the shampoo, the conditioners also may contain one or more optional foaming agents, foam stabilizers, preservatives and/or chelating agents, antimicrobials, fragrances, colorants, opacifiers, pearlizing agents, moisturizing agents, medicaments, buffers and/or pH modifiers, and UV absorbers, for further improving performance, marketability, or aesthetics.

The shampoos and conditioners of the present invention can be made using conventional techniques. While mixing the components together with agitation is generally satisfactory, application of gentle heating may aid emulsification. The pH of the present compositions is not critical and may vary with the particular surfactant(s) selected. Typically, the pH may range between about 4.5 to 8.5, preferably between about 5.5 to 6.0.

The following examples are intended only to further illustrate the invention and are not intended to limit the scope of the invention which is defined by the claims.

EXAMPLE 1

The performance of a leading market shampoo was compared with the same formulation containing added estolides. Estolides for use herein were prepared from oleic acid and from meadowfoam oil by perchloric acid catalysis as described by Isbell and Kleiman (1994, J. Amer. Oil Chem. Soc., 71(4):379–383, and U.S. patent application Ser. No. 08/382,554, respectively. Test shampoo formulations were made by adding 4% by weight of either oleic estolide or meadowfoam estolide to the leading market shampoo, with all other components held at a constant weight percent. Shampoos with and without estolides were then compared using half-head tests. Eleven properties were evaluated for each shampoo formulation including flash foam, lather, foam rinseability, rinsability, wet feel, detangling, dry comb feel, static, style management, shine, and body. The results are shown in Table 1. The estolide containing formulations were rated as nearly twice as good as the market shampoo in seven of the tests, slightly better in one test, and equal in the three remaining tests. Categories of outstanding performance significantly improved by addition of estolides included rinseability, wet feel, detangling, dry comb feel, style management, shine, and body.

It is understood that the foregoing detailed description is given merely by way of illustration and that modifications and variations may be made therein without departing from the spirit and scope of the invention.

TABLE 1

Table of Half-Head Tests for Estolide Against a Leading Shampoo Formulation

| Test | Market Shampoo | Meadowfoam Estolide | Market Shampoo | Oleic Estolide | Best | Worst |
|---|---|---|---|---|---|---|
| Flash Foam | 12 | 12 | 12 | 12 | 11 | 99 |
| Lather | 12 | 12 | 12 | 12 | 11 | 99 |
| Foam Density | 19 | 16 | 14 | 11 | 11 | 99 |
| Rinseability | 20 | 12 | 22 | 13 | 11 | 99 |
| Wet Feel | 23 | 13 | 18 | 11 | 11 | 99 |
| Detangling | 24 | 13 | 23 | 13 | 11 | 99 |
| Dry Comb Feel | 23 | 12 | 20 | 11 | 11 | 99 |
| Static | 11 | 11 | 17 | 11 | 11 | 99 |
| Style Management | 21 | 12 | 21 | 12 | 11 | 99 |
| Shine | 21 | 11 | 22 | 12 | 11 | 99 |
| Body | 22 | 13 | 18 | 11 | 11 | 99 |

Market shampoo is the same formulation used in both half-head test trials
Scores shown are the sum of the ratings of all eleven test subjects

We claim:

1. In a shampoo composition comprising a surfactant cleansing agent, a thickener, and water, wherein the improvement comprises adding fatty acid estolide.

2. The shampoo composition of claim 1 wherein said estolide has the formula:

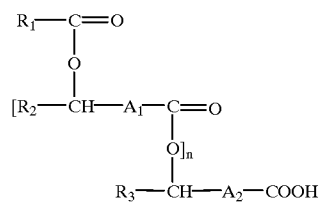

wherein $R_1$, $R_2$ and $R_3$ are independently selected from hydrocarbons which may be saturated or unsaturated, branched or straight chain, $A_1$ and $A_2$ are independently selected from hydrocarbons which may be saturated or unsaturated, branched or straight chain, and n is an integer greater than or equal to 0, usually 0 or 1.

3. The shampoo composition of claim 2 wherein $R_1$ is $CH_3(CH_2)_{13}CH=CH(CH_2)_3-$, $R_2$ and $R_3$ are both $CH_3(CH_2)_{14}-$, $A_1$ and $A_2$ are both $-(CH_2)_3-$, and n is between 0–10.

4. The shampoo composition of claim 2 wherein $R_1$ is $CH_3(CH_2)_7CH=CH(CH_2)_7-$, $R_2$ and $R_3$ are both $CH_3(CH_2)_8-$, $A_1$ and $A_2$ are both $-(CH_2)_7-$, and n is between 0–10.

5. The shampoo composition of claim 1 wherein said estolide is present at a concentration effective to improve one or more of rinseability, wet feel, detangling, dry comb feel, style management, shine, or body.

6. The shampoo composition of claim 1 wherein the concentration of estolide is between about 1 to 8% by weight of said composition.

7. The shampoo composition of claim 5 wherein the concentration of estolide is between about 2 to 6% by weight of said composition.

8. The shampoo composition of claim 1 wherein said surfactant cleansing agent is selected from the group consisting of an anionic surfactant, a nonionic surfactant, an amphoteric surfactant, a zwitterionic surfactant, and mixtures thereof.

9. The shampoo composition of claim 7 wherein said surfactant is selected from the group consisting of ammonium lauryl ether sulfate and coconut diethanolamide.

10. The shampoo composition of claim 1 wherein said thickener is present in an amount effective to increase viscosity to greater than or equal to about 1200 cp.

11. The shampoo composition of claim 1 further comprising one or more agents selected from the group consisting of conditioners, foaming agents, foam stabilizers, preservatives, chelating agents, antimicrobials, fragrances, colorants, opacifiers, pearlizing agents, moisturizing agents, medicaments, buffers, pH modifiers, and UV absorbers.

12. A hair conditioner composition comprising a hair conditioning agent, a thickener, and water, wherein the improvement comprises adding fatty acid estolide.

13. The conditioner composition of claim 12 wherein said estolide has the formula:

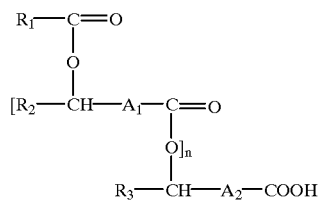

wherein $R_1$, $R_2$ and $R_3$ are independently selected from hydrocarbons which may be saturated or unsaturated, branched or straight chain, $A_1$ and $A_2$ are independently selected from hydrocarbons which may be saturated or unsaturated, branched or straight chain, and n is an integer greater than or equal to 0, usually 0 or 1.

14. The conditioner composition of claim 13 wherein $R_1$ is $CH_3(CH_2)_{13}CH=CH(CH_2)_3-$, $R_2$ and $R_3$ are both $CH_3(CH_2)_{14}-$, $A_1$ and $A_2$ are both $-(CH_2)_3-$, and n is between 0–10.

15. The conditioner composition of claim 13 wherein $R_1$ is $CH_3(CH_2)_7CH=CH(CH_2)_7-$, $R_2$ and $R_3$ are both $CH_3(CH_2)_8-$, $A_1$ and $A_2$ are both $-(CH_2)_7-$, and n is between 0–10.

16. The conditioner composition of claim 12 wherein said estolide is present at a concentration effective to improve one or more of rinseability, wet feel, detangling, dry comb feel, style management, shine, or body.

17. The conditioner composition of claim 12 wherein the concentration of estolide is between about 1 to 8% by weight of said composition.

18. The conditioner composition of claim 17 wherein the concentration of estolide is between about 2 to 6% by weight of said composition.

19. The conditioner formulation of claim 12 wherein said conditioning agent is selected from the group consisting of silicones, cationic surfactants, quaternary ammonium compounds, and synthetic cationic polymers.

20. The conditioner composition of claim 12 wherein said thickener is present in an amount effective to increase viscosity to greater than or equal to about 1200 cp.

21. The conditioner composition of claim 12 further comprising one or more agents selected from the group consisting of foaming agents, foam stabilizers, preservatives, chelating agents, antimicrobials, fragrances, colorants, opacifiers, pearlizing agents, moisturizing agents, medicaments, buffers, pH modifiers, and UV absorbers.

* * * * *